(12) United States Patent
Hsu et al.

(10) Patent No.: US 10,092,709 B2
(45) Date of Patent: Oct. 9, 2018

(54) SAFETY SYRINGE AND NEEDLE AND NEEDLE SEAT RETRACTING DEVICE OF SAFETY SYRINGE

(71) Applicants: Pei-Yang Hsu, Taichung (TW); Pei-Hsin Hsu, Taichung (TW); Wei-Ni Hsu, Taichung (TW)

(72) Inventors: Pei-Yang Hsu, Taichung (TW); Pei-Hsin Hsu, Taichung (TW); Wei-Ni Hsu, Taichung (TW)

( * ) Notice: Subject to any disclaimer, the term of this patent is extended or adjusted under 35 U.S.C. 154(b) by 468 days.

(21) Appl. No.: 14/747,771

(22) Filed: Jun. 23, 2015

(65) Prior Publication Data
US 2015/0374928 A1   Dec. 31, 2015

(30) Foreign Application Priority Data
Jun. 25, 2014   (TW) .............................. 103121993 A

(51) Int. Cl.
*A61M 5/32* (2006.01)
*A61M 5/31* (2006.01)

(52) U.S. Cl.
CPC ........ *A61M 5/3232* (2013.01); *A61M 5/3137* (2013.01); *A61M 5/3234* (2013.01); *A61M 2005/3231* (2013.01); *A61M 2005/3239* (2013.01); *A61M 2005/3242* (2013.01)

(58) Field of Classification Search
CPC .............. A61M 5/3232; A61M 5/3234; A61M 5/3137; A61M 2005/3242; A61M 2005/3239; A61M 2005/3231; A61M 2005/3241; A61M 2005/3238; A61M 2005/3258; A61M 2005/3279
See application file for complete search history.

(56) References Cited

U.S. PATENT DOCUMENTS

2006/0253074 A1* 11/2006 Thayer ................ A61M 5/3234
                                                      604/110
2007/0066936 A1*  3/2007 Lam .................... A61M 5/3234
                                                      604/110

* cited by examiner

*Primary Examiner* — Bradley J Osinski
*Assistant Examiner* — Hamza Darb
(74) *Attorney, Agent, or Firm* — patenttm.us

(57) ABSTRACT

A safety syringe has a barrel, a pushing element, a retracting element, and a needle group. The barrel is hollow and has a needle-group mounting end, an operating grip end, and a barrel lumen. The pushing element is retractably mounted in the barrel lumen and has a pushrod chamber. The retracting element is airtightly and slidably mounted in the pushrod chamber. The needle group is connected to the needle-group mounting end of the barrel. The present invention can pull the retracting element to move relative to the pushing element to form a low pressure condition in the pushrod chamber as a vacuum status. After the injection, a vacuum attraction force in the pushrod chamber can retract the used needle group into the pushrod chamber for safe use of the safety syringe.

15 Claims, 15 Drawing Sheets

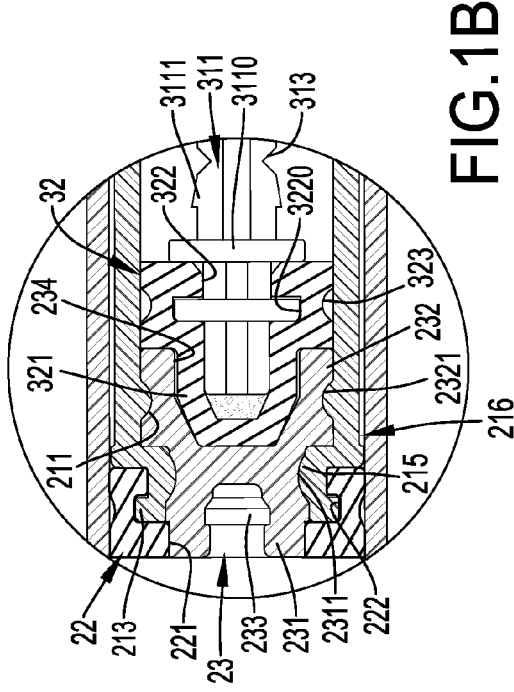
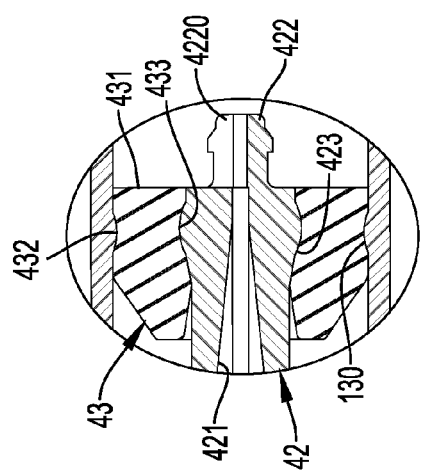
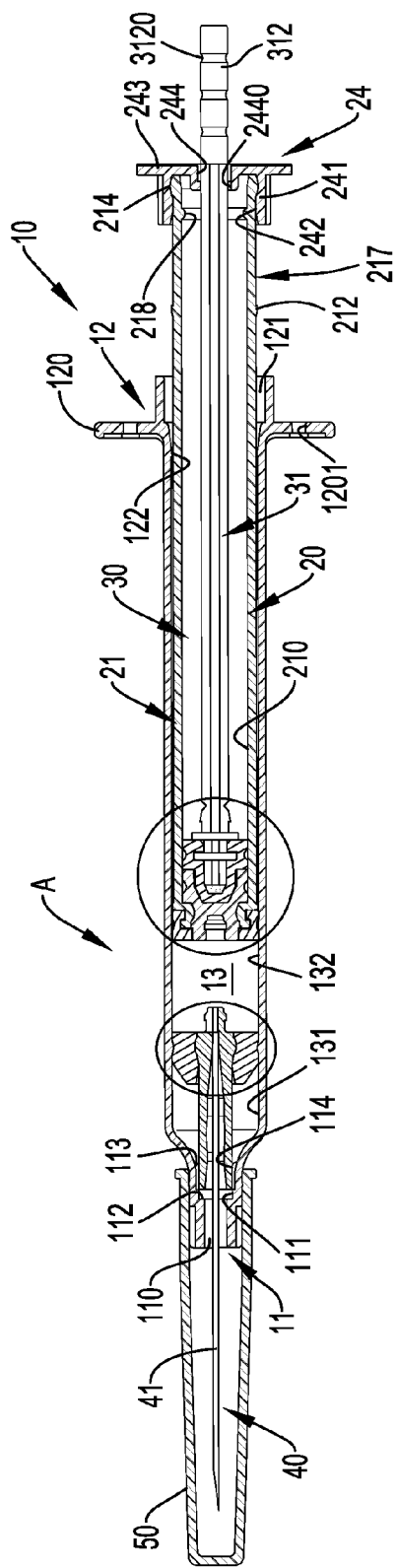

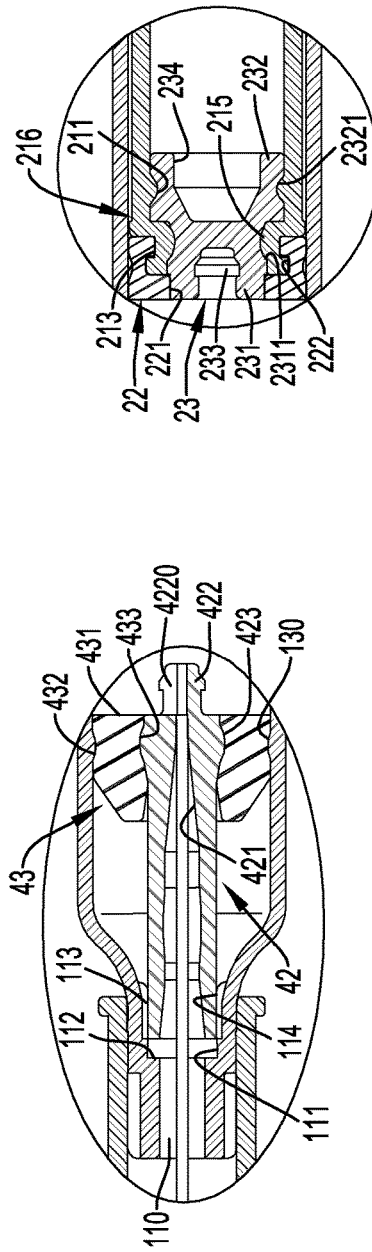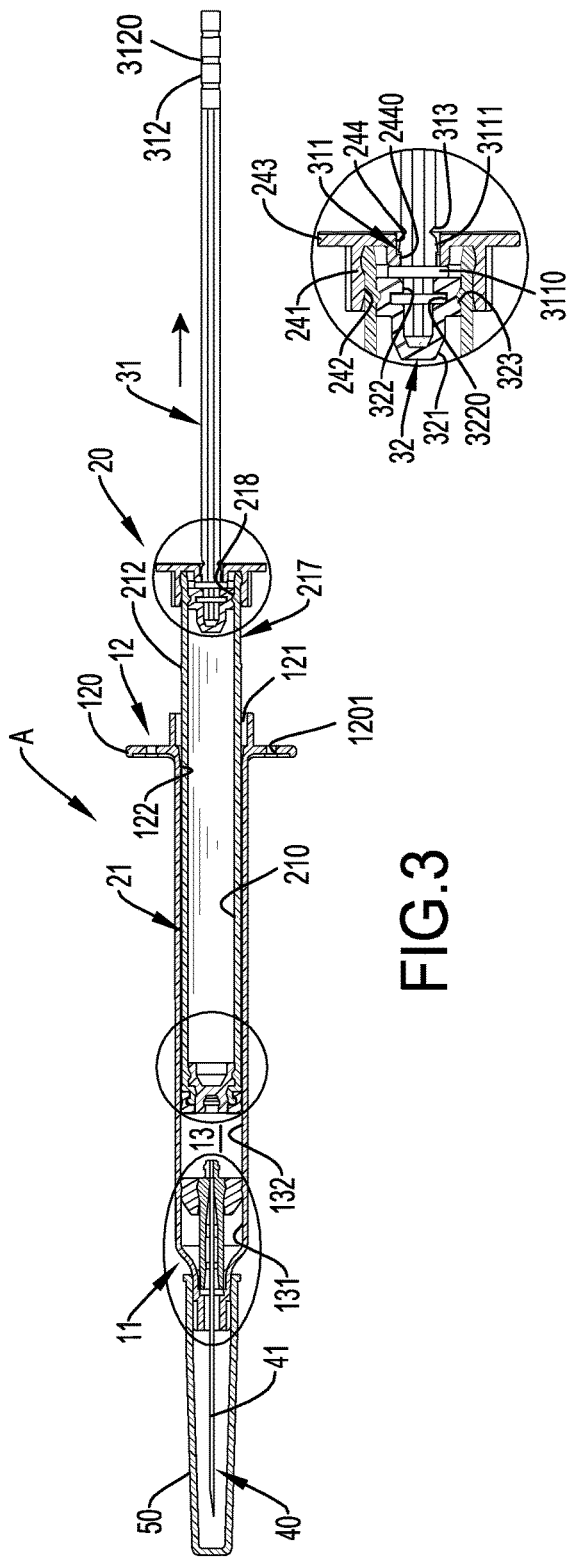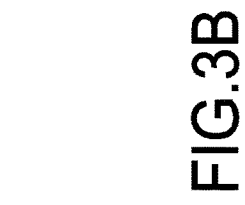

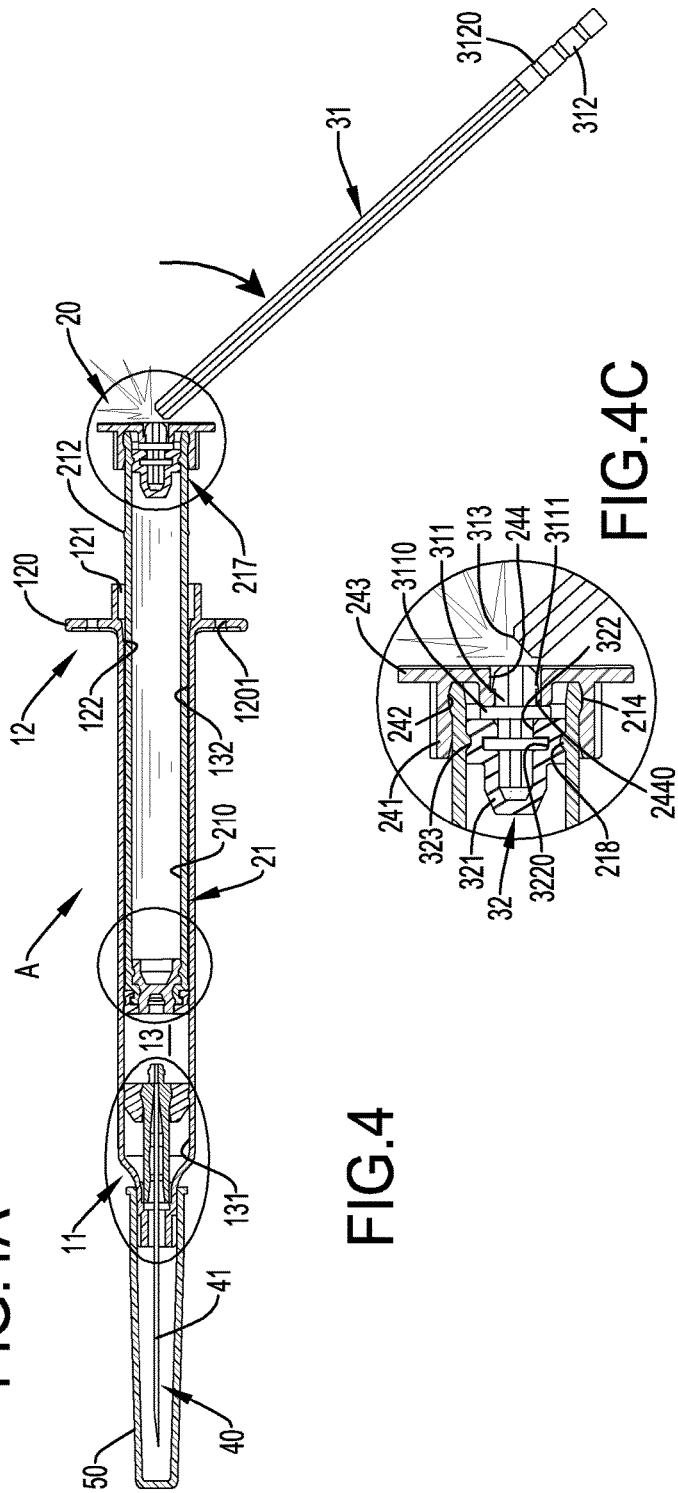

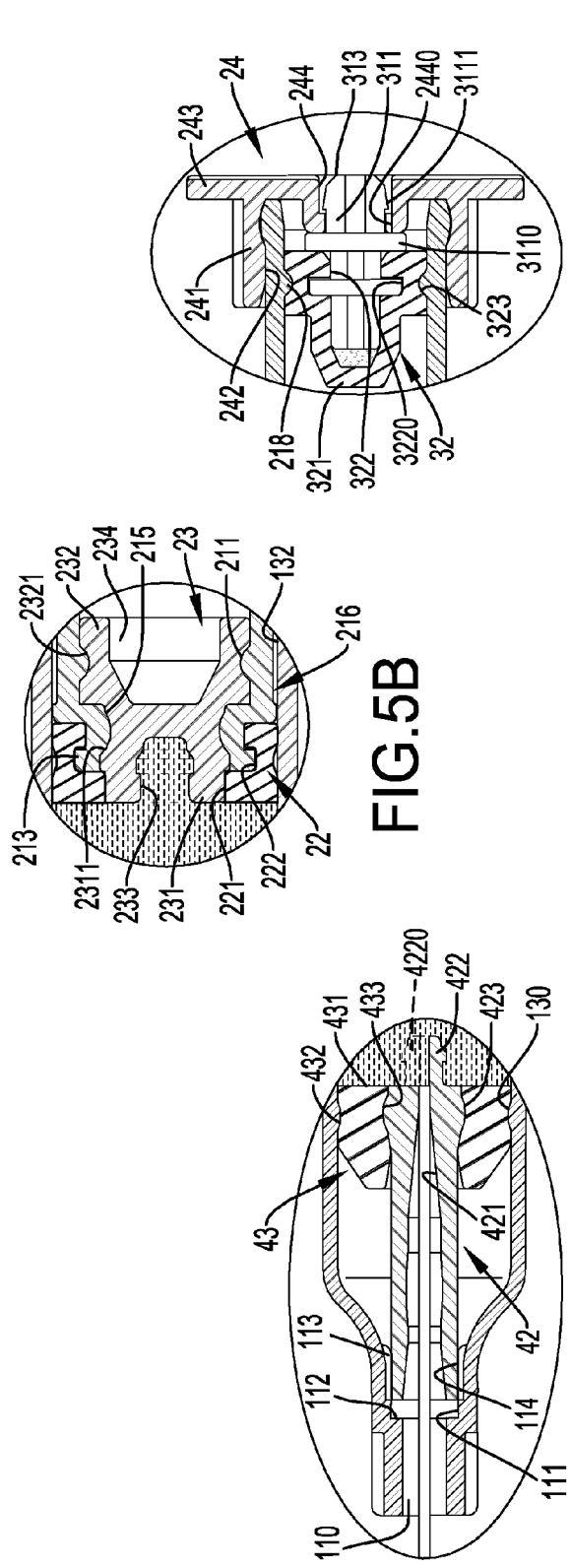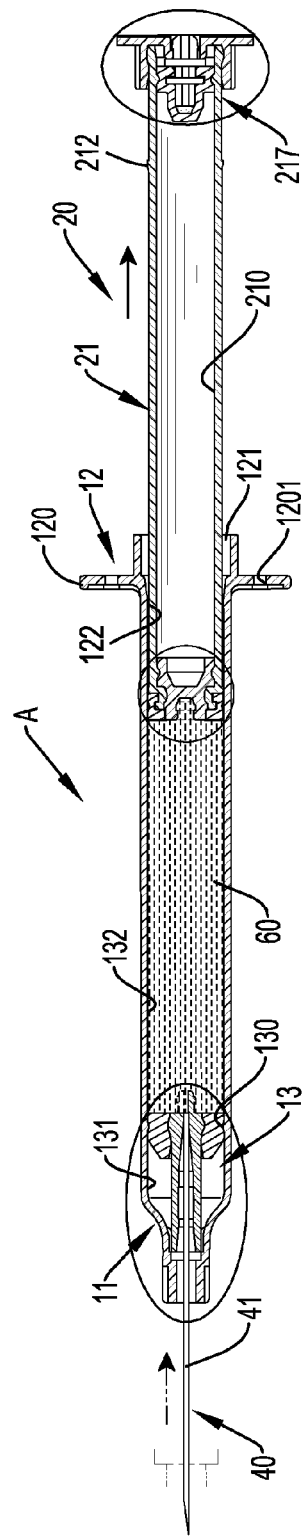

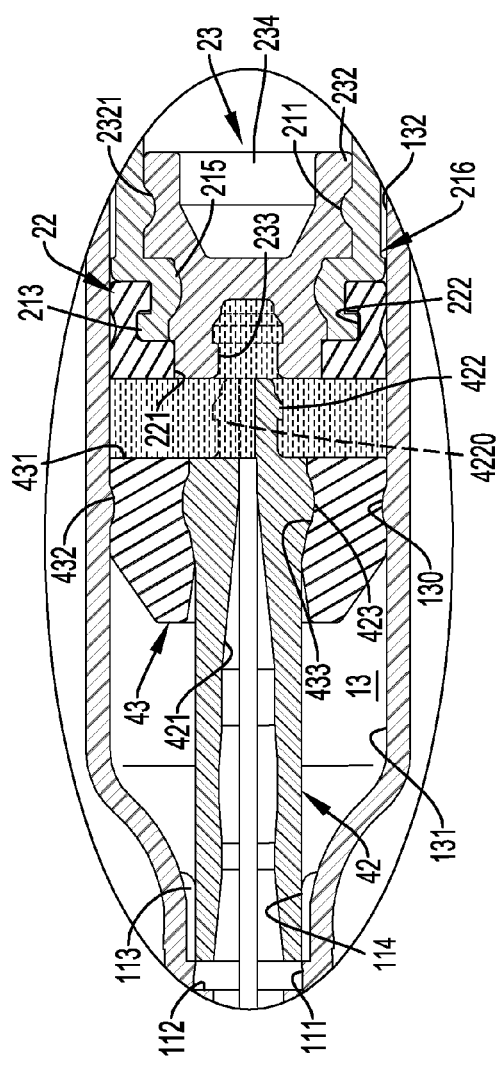

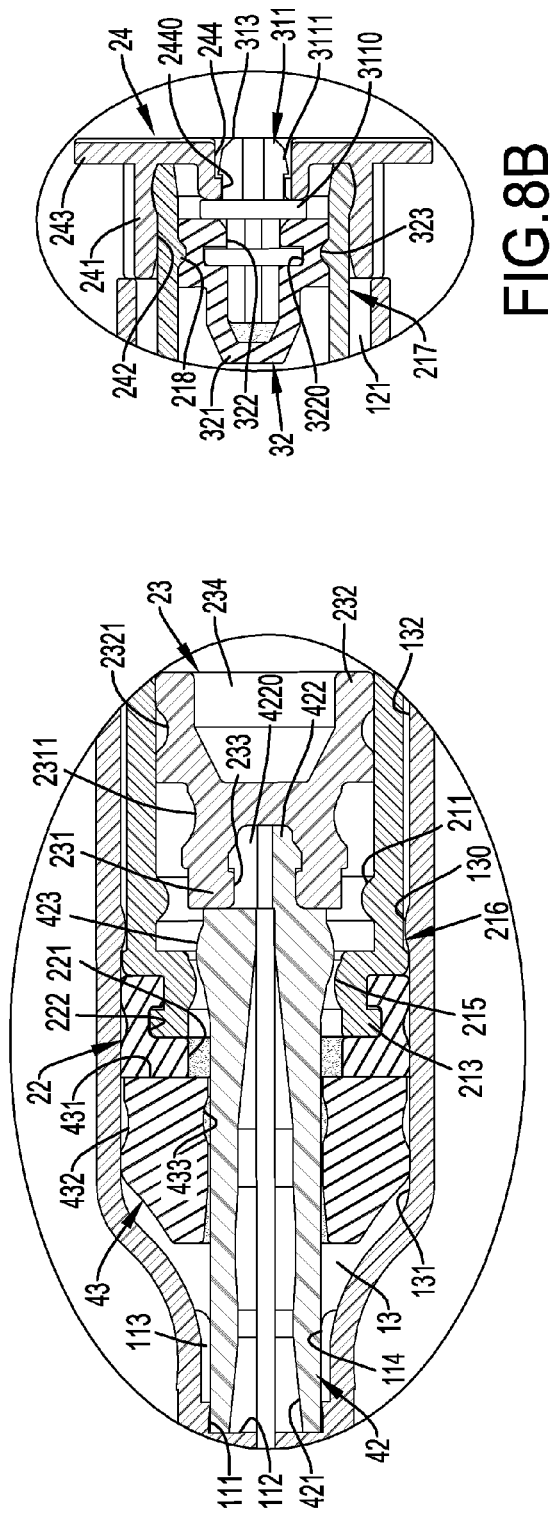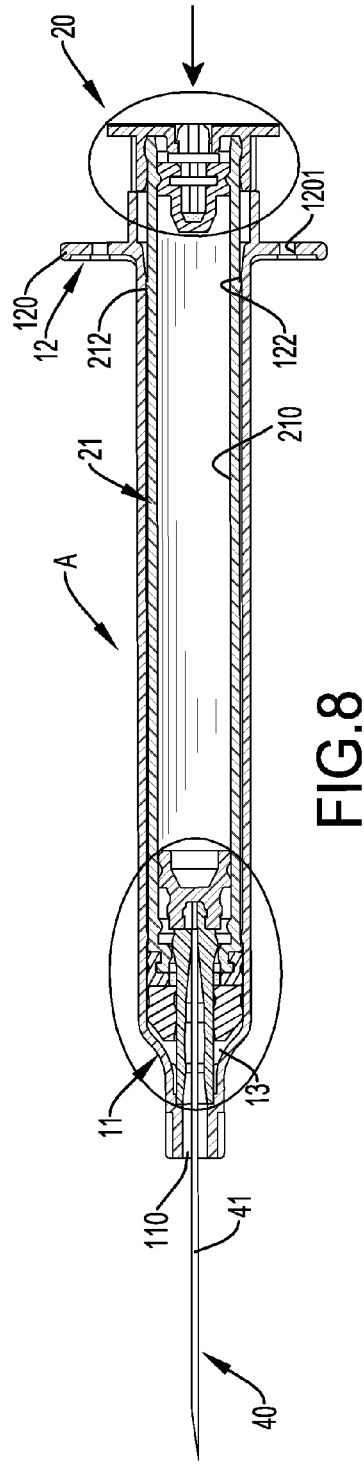
FIG.8A  FIG.8B  FIG.8

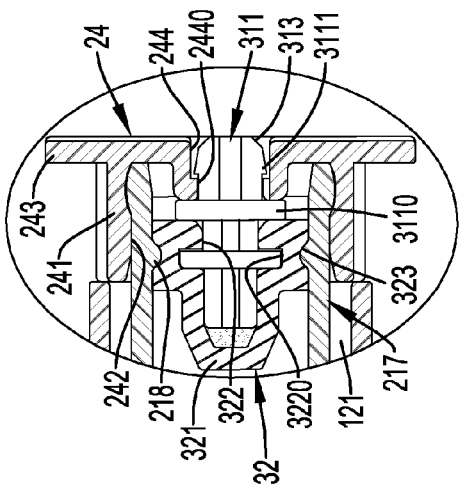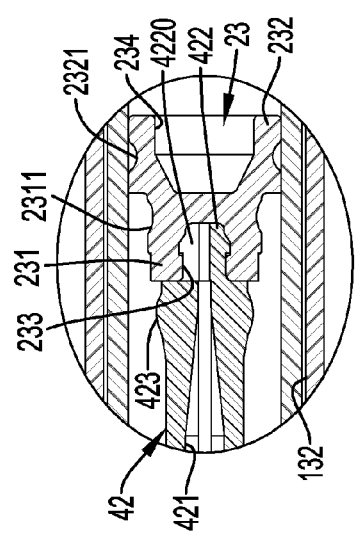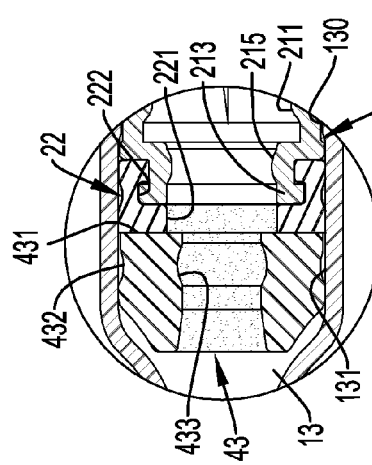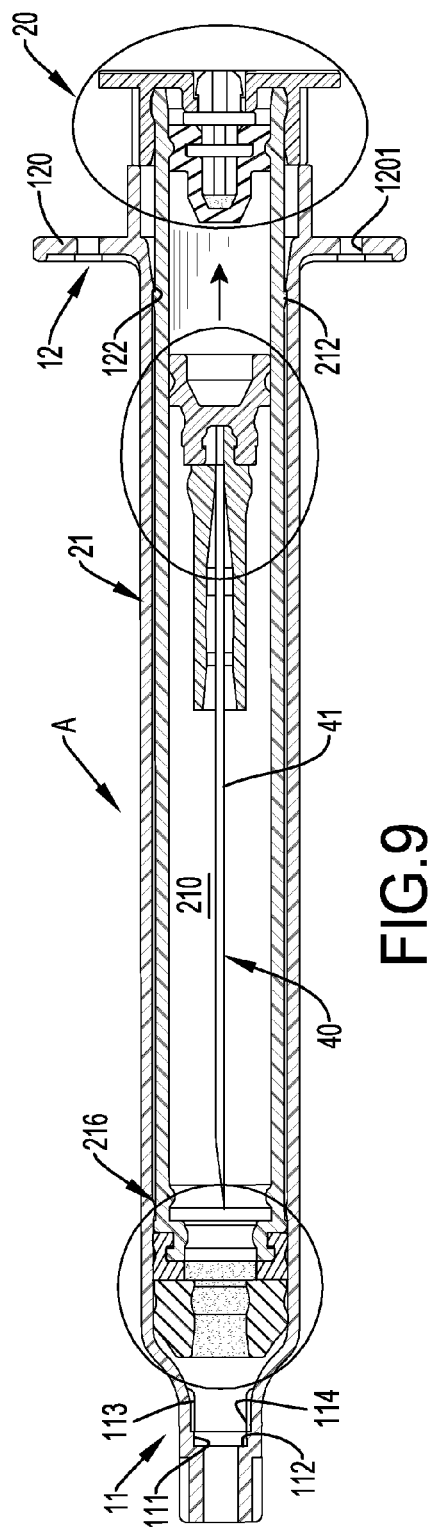

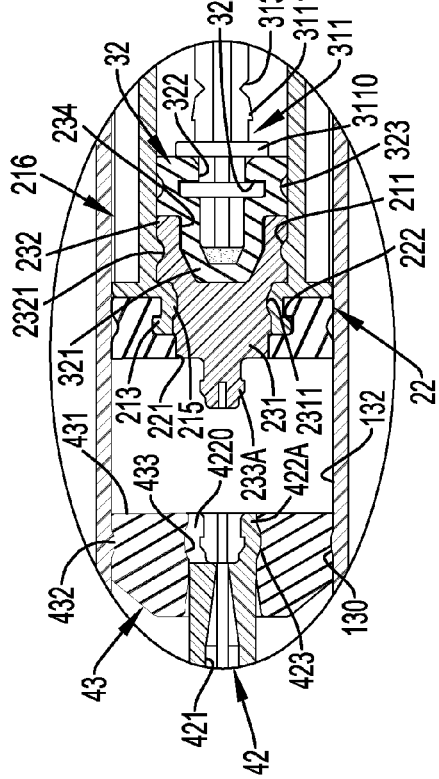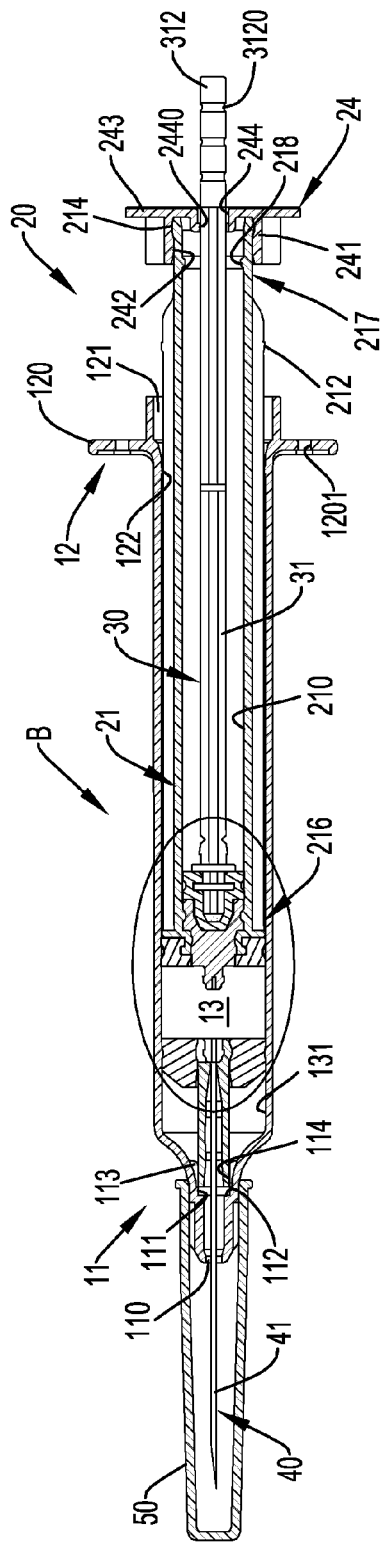

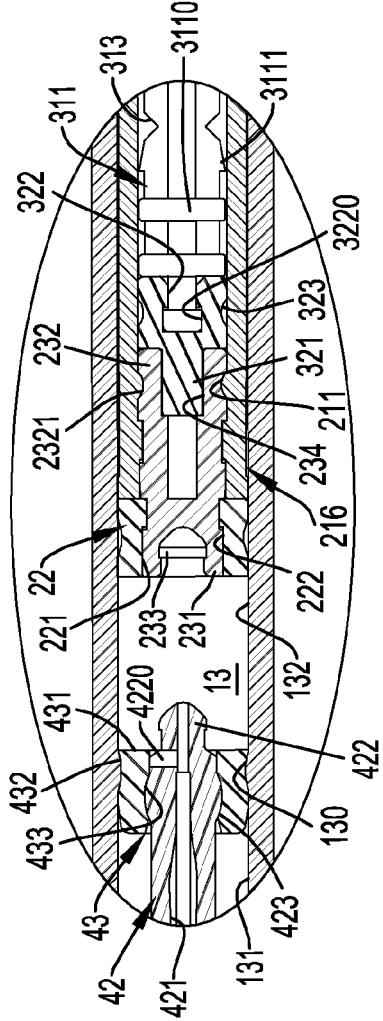
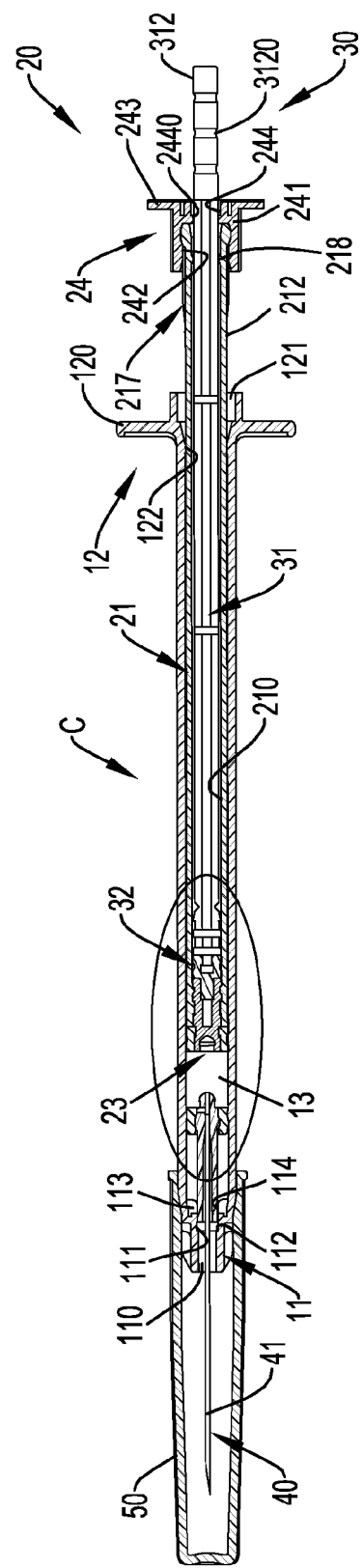
FIG. 12A
FIG. 12

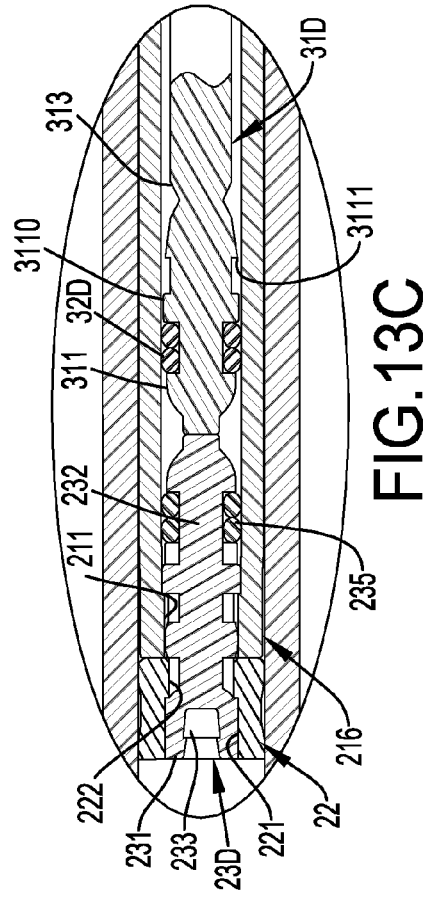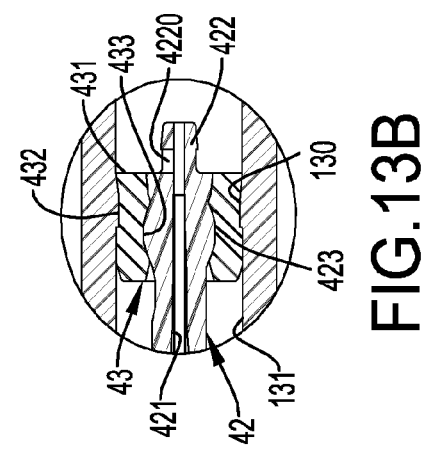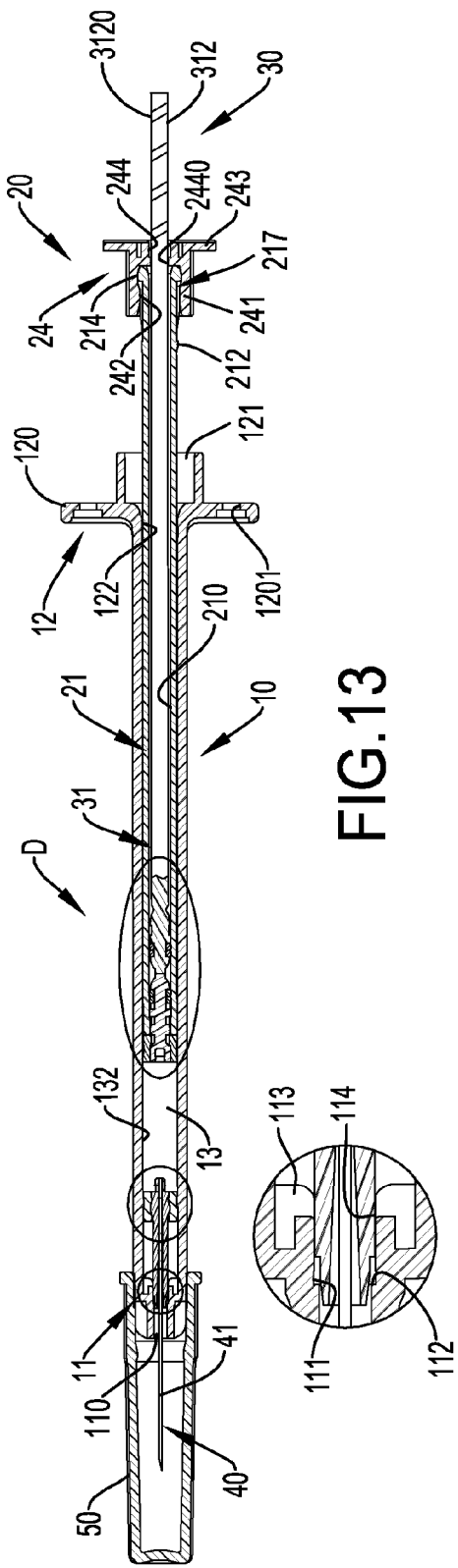

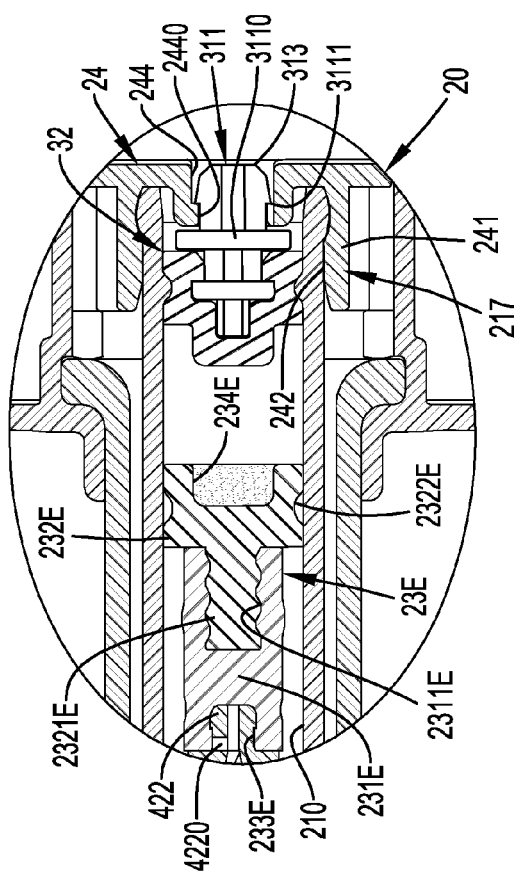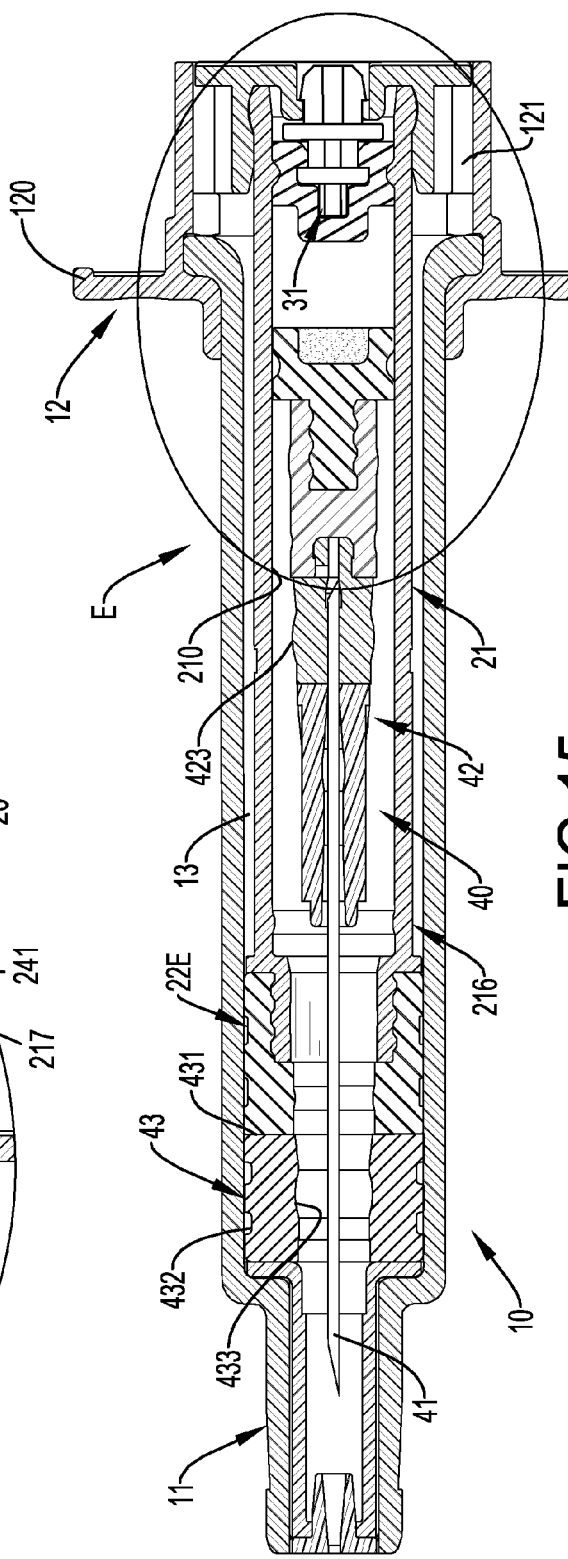

SAFETY SYRINGE AND NEEDLE AND NEEDLE SEAT RETRACTING DEVICE OF SAFETY SYRINGE

BACKGROUND OF THE INVENTION

1. Field of the Invention

The present invention relates to medical supplies, and more particularly to a safety syringe that can be operated to remove a used needle safely, can prevent a user from being injured by the used needle, and can be manufactured in a comparatively easier process.

2. Description of Related Art

Medical personnel are often stabbed by a contaminated needle of a used syringe when mounting a needle cap around the contaminated needle, and this may lead to needle stick injury and subsequent blood born pathogen infection accidents. After a conventional syringe is used, the needle cap must be mounted around the used needle, and the used syringe was thrown into a collection container or was collected for proper disposal according to the provisions to avoid a similar situation from happening again.

In order to improve the safety of using the conventional syringes, the inventors in accordance with the present invention have painstakingly researched and applied various types with innovative designs of safety syringe. By the configuration of an interior of a barrel of the inventors' safety syringe, a used needle can be retracted into the interior of the barrel for storage after injection, and this can reduce the chance of contacting the contaminated needle for users and also can reduce the fear of the medical personnel when using the syringes.

However, the inventors are not satisfied with the application of the above-mentioned safety syringe, are still continuously committed to the technical enhancement of the safety syringe, and are painstakingly doing researches to simplify the internal structure and manufacturing process of the safety syringe and to provide a novel technology that can increase the security, stability, and smoothness of using the safety syringe, and this can raise the medical technology to a higher level.

To overcome the shortcomings, the present invention tends to provide a safety syringe to mitigate or obviate the aforementioned problems.

SUMMARY OF THE INVENTION

The main objective of the invention is to provide a safety syringe that can be operated to remove a used needle safely, can prevent a user from being injured by the used needle, and can be manufactured easily.

The safety syringe in accordance with the present invention has a barrel, a pushing element, a retracting element, and a needle group. The barrel is hollow and has a needle-group mounting end, an operating grip end, and a barrel lumen. The pushing element is retractably mounted in the barrel lumen and has a pushrod chamber. The retracting element is airtightly and slidably mounted in the pushrod chamber. The needle group is connected to the needle-group mounting end of the barrel. The present invention can pull the retracting element to move relative to the pushing element to form a low pressure condition in the pushrod chamber as a vacuum driving force. After the injection, a vacuum attraction force in the pushrod chamber can retract the used needle group into the pushrod chamber for using the safety syringe safely.

Other objects, advantages and novel features of the invention will become more apparent from the following detailed description when taken in conjunction with the accompanying drawings.

BRIEF DESCRIPTION OF THE DRAWINGS

FIG. 1 is a cross sectional side view of a first embodiment of a safety syringe in accordance with the present invention;

FIG. 1A is an enlarged cross sectional side view of the safety syringe in FIG. 1;

FIG. 1B is another enlarged cross sectional side view of the safety syringe in FIG. 1;

FIG. 3 is an operational and cross sectional side view of the safety syringe in FIG. 1, showing a pulling rod is pulled;

FIGS. 3A to 3C are enlarged and cross sectional side views of the safety syringe in FIG. 3;

FIG. 4 is an operational and cross sectional side view of the safety syringe in FIG. 3, showing the pulling rod is broken;

FIGS. 4A to 4C are enlarged and cross sectional side views of the safety syringe in FIG. 4;

FIG. 5 is an operational and cross sectional side view of the safety syringe in FIG. 4, showing drug is drawn by a pushing element of the safety syringe;

FIGS. 5A to 5C are enlarged and cross sectional side views of the safety syringe in FIG. 5;

FIG. 6 is an operational and cross sectional side view of the safety syringe in FIG. 5, showing drug is injected into a patient by the pushing element;

FIGS. 6A and 6B are operational and cross sectional side views of the safety syringe in FIG. 6;

FIG. 8 is an operational and cross sectional side view of the safety syringe in FIG. 7, showing the needle seat fixing ring is disengaged from a needle seat;

FIGS. 8A and 8B are enlarged and cross sectional side views of the safety syringe in FIG. 8;

FIG. 9 is an operational and cross sectional side view of the safety syringe in FIG. 8, showing a used needle is retracted into a pushrod chamber by outside air pressure;

FIGS. 9A to 9C are enlarged and cross sectional side views of the safety syringe in FIG. 9;

FIG. 11 is a cross sectional side view of a third embodiment of a safety syringe in accordance with the present invention;

FIG. 11A is an enlarged and cross sectional side view of the safety syringe in FIG. 11;

FIG. 12 a cross sectional side view of a fourth embodiment of a safety syringe in accordance with the present invention;

FIG. 12A is an enlarged and cross sectional side view of the safety syringe in FIG. 12;

FIG. 13 a cross sectional side view of a fifth embodiment of a safety syringe in accordance with the present invention;

FIGS. 13A to 13C are enlarged and cross sectional side views of the safety syringe in FIG. 13;

FIG. 15 is an operational and cross sectional side view of the safety syringe in FIG. 14; and FIG. 15A is an enlarged and cross sectional side view of the safety syringe in FIG. 15.

DETAILED DESCRIPTION OF PREFERRED EMBODIMENT

With reference to FIGS. 1, 1A, 1B, and 2, a first embodiment of a safety syringe A in accordance with the present invention comprises an injection volume, a barrel 10, a needle and needle seat retracting device, a needle group 40, and a needle cap 50. The injection volume of the safety syringe A is about 3 cubic centimetes (C.C.). In addition, the needle and needle seat retracting device comprises a pushing element 20 and a retracting element 30

Figure 2:
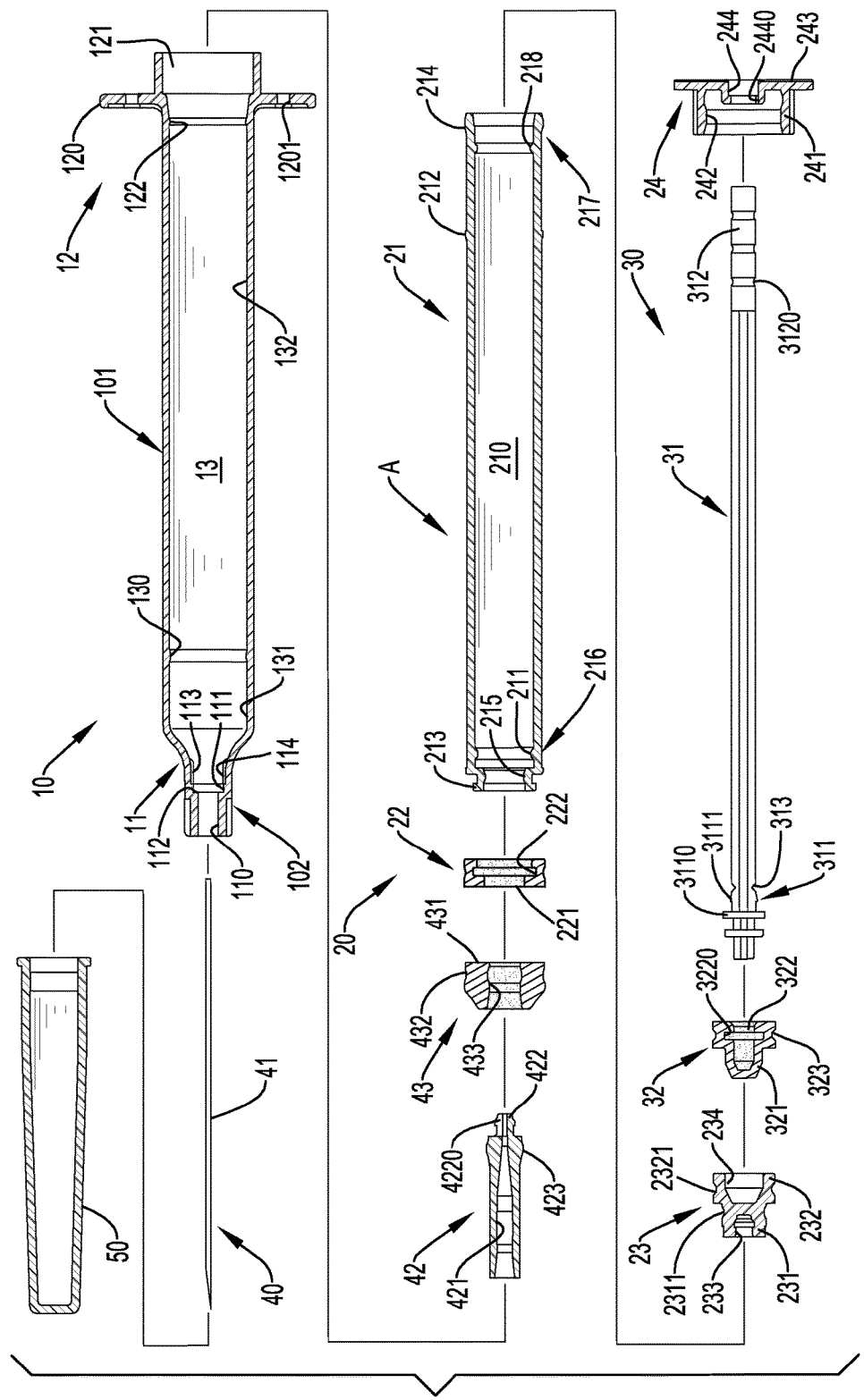
FIG. 2 is an exploded cross sectional side view of the safety syringe in FIG. 1.

With reference to FIGS. 1, 1A, 1B, and 2, firstly, the left and right directions in FIGS. 1 and 2 are respectively defined as the front and rear directions in the following description. The barrel 10 is a hollow cylinder, extends along an axis from front to rear direction, and has a large-diameter section 101 and a small-diameter section 102. The large-diameter section 101 has a front end and a rear end. The small-diameter section 102 is in a tapered-shape and is formed on and protrudes from the front end of the large-diameter section 101. In addition, the front end of the large-diameter section 101 that is formed with the small-diameter section 102 can be defined as a needle-group mounting end 11, and the rear end of the large-diameter section 101 that is opposite to the needle-group mounting end 11 can be defined as an operating grip end 12. The barrel 10 has a barrel lumen 13 formed in the large-diameter section 101 for suction, storage, and injection of drug.

Wherein, the small-diameter section 102 has a needle-extending hole 110, a needle-seat holding hole 114, an abutting step flange 112, multiple ribs 113, and a triggering facilitating gap 111. The needle-extending hole 110 is formed through the small-diameter section 102, communicates with the barrel lumen 13, and has an inner diameter. The needle-seat holding hole 114 is formed in an annular wall of the small-diameter section 102 behind the needle-extending hole 110, and has an inner diameter larger than the inner diameter of the needle-extending hole 110. The abutting step flange 112 is formed in the annular wall of the small-diameter section 102 between the needle-extending hole 110 and the needle-seat holding hole 114.

The ribs 113 are formed on and protrude from the annular wall of the small-diameter section 102 at a rear end of the needle-seat holding hole 114 to provide an assisting holding effect to the needle group 40. The triggering facilitating gap 111 is formed in the small-diameter section 102 between the abutting step flange 112 and a front end of the needle-seat holding hole 114 to provide a facilitating effect of triggering an initial movement of the needle group 40 after use of the safety syringe A. The needle group 40 is securely held and positioned in the barrel 10 by the needle-seat holding hole 114, the ribs 13, and the needle-group mounting end 11.

The barrel 10 has a hand-grip segment 120 formed on and protruding from an external wall of the operating grip end 12. The hand-grip segment 120 has multiple label holes 1201 formed the hand-grip segment 120 and spaced apart at intervals for connecting a label or a name tag. The operating grip end 12 has a rear end and an entry end 121 formed through the rear end of the operating grip end 12. The barrel 10 has a protruding ring 122 annularly formed on and protruding from an inner wall of the barrel 10 adjacent to the operating grip end 12. The barrel lumen 13 has an engaging flange 130, a needle-seat positioning segment 131, and a moving segment 132. The engaging flange 130 is formed on and protrudes from the inner wall of the barrel 10 adjacent to the needle-group mounting end 11 to divide the barrel lumen 13 into two sections. The needle-seat positioning segment 131 is formed in one of the two sections of the barrel lumen 13 that is adjacent to the needle-group mounting end 11. The moving segment 132 is formed in the other section of the barrel lumen 13 opposite to the needle-group positioning segment 131.

The pushing element 20 is airtightly and slidably mounted in the barrel lumen 13 of the barrel 10, and has a pushing rod 21, an outer airtight stopper 22, an inner airtight stopper 23, and an end cover 24. The pushing rod 21 is a hollow straight tube, and is formed cylindrically along an axis through a front end and a rear end of the pushing rod 21. The pushing rod 21 has a front drug pushing end 216, a rear operating end 217, a pushrod chamber 210, a first interior ring 211, a second interior ring 218, an outer ring 212, a mounting segment 213, an engaging edge 214, and an inner ring 215.

The front drug pushing end 216 is formed on the front end of the pushing rod 21. The mounting segment 213 is formed in the front drug pushing end 216 and has an inner diameter smaller than a diameter of the pushrod chamber 210. The rear operating end 217 is formed on the rear end of the pushing rod 21, is opposite to the front drug pushing end 216, and extends out of the barrel lumen 13. The front drug pushing end 216 of the pushing rod 21 is airtightly and slidably mounted in the moving segment 132 of the barrel lumen 13. Preferably, the front drug pushing end 216 has a screwed segment. The pushrod chamber 210 is formed in the pushing rod 21 between the front end and the rear end of the pushing rod 21. The first interior ring 211 is annularly formed on and protrudes from an inner wall of the pushing rod 21 adjacent to the front drug pushing end 216. The second interior ring 218 is annularly formed on and protrudes from the inner wall of the pushrod chamber 210 of the pushing rod 21 adjacent to the rear operating end 217. The outer ring 212 is annularly formed on and protrudes from an outer wall of the pushing rod 21 adjacent to the rear operating end 217, and selectively engages the protruding ring 122 of the barrel 10 to prevent the pushing rod 21 separating from the barrel lumen 13 after injection. The mounting segment 213 is step-shaped and is formed around the front drug pushing end 216. The engaging edge 214 is annularly formed on the outer wall of the pushing rod 21 at the rear end of the pushing rod 21. The inner ring 215 is annularly formed in an inner wall of the mounting segment 213.

The outer airtight stopper 22 is airtightly connected to the front drug pushing end 216, is mounted around the mounting segment 213 of the pushing rod 21, and has a center, a front side, a rear side, an engaging hole 221 and an annular slot 222. The engaging hole 221 is formed through the front side and the rear side of the outer airtight stopper 22 at the center of the outer airtight stopper 22, and is disposed around the mounting segment 213 of the pushing rod 21. The annular slot 222 is annularly formed in an inner wall of the engaging hole 221 and engages the mounting segment 213. Preferably, the outer airtight stopper 22 is airtightly screwed with the screwed segment of the front drug pushing end 216.

The inner airtight stopper 23 is a step block, is airtightly and securely mounted in the front drug pushing end 216 and extends into the pushrod chamber 210 of the pushing rod 21, and is airtightly connected to the outer airtight stopper 22. The inner airtight stopper 23 has a front end, a rear end, a protruding segment 231, an engaging segment 232, a connecting segment 233, and an unplug recess 234. The protruding segment 231 is formed on the front end of the inner airtight stopper 23 and has a diameter, an outer wall, and a concave groove 2311. The concave groove 2311 is annularly formed on the outer wall of the protruding segment 231. The inner airtight stopper 23 is airtightly and securely connected to the front drug pushing end 216 and is airtightly mounted through the engaging hole 221 of the outer airtight stopper 22, and the concave groove 2311 airtightly engages the inner ring 215 of the mounting segment 213. The engaging segment 232 extends into the pushrod chamber 210, is formed on the rear end of the inner airtight stopper 23, is formed with the protruding segment 231, and has a diameter, an outer wall and an annular recess 2321. The diameter of the engaging segment 232 is larger than the diameter of the protruding segment 231. The annular recess 2321 is annularly formed on the outer wall of the engaging segment 232 and airtightly engages the first interior ring 211 of the pushing rod 21. Then, the inner airtight stopper 23 can be securely mounted in the pushing rod 21 and can be airtightly connected to the outer airtight stopper 22. The connecting segment 233 is centrically grooved and is formed in a front side of the protruding segment 231. The unplug recess 234 is centrically formed in the engaging segment 232.

The end cover 24 is securely mounted on the rear operating end 217 of the pushing rod 21 and has a body 241, a mounting recess 242, a cover bottom 243, and a holding tube 244. The body 241 is cylindrical and has an inner wall, a front side, and a rear side. The mounting recess 242 is formed in the inner wall of the end cover 24 between the front side and the rear side of the end cover 24. The cover bottom 243 is formed on and protrudes from the rear side of the end cover 24 to close the mounting recess 242, and has an inner side. The holding tube 244 is centrically formed on and axially protrudes from the inner side of the cover bottom 243, is formed through the cover bottom 243, and has an inner end and a retaining flange 2440. The retaining flange 2440 is formed on and protrudes from the inner end of the holding tube 244.

With reference to FIGS. 1, 1B, and 2, the retracting element 30 is airtightly and slidably mounted in the pushrod chamber 210 of the pushing rod 21 and has a pulling rod 31 and an airtight spigot 32.

The pulling rod 31 is an elongated rod with multiple protruding ribs formed on an outer surface of the pulling rod 31, and has a front end, a rear end, an engaging end 311, a depressed gap 313, and a gripping end 312. The engaging end 311 of the pulling rod 31 is formed on the front end of the pulling rod 31, engages the airtight spigot 32, and extends rearward in and beyond the pushrod chamber 210 to enable the airtight spigot 32 being adjacent to the inner airtight stopper 23. The engaging end 311 has an outer surface, multiple engaging panels 3110, and an engaged flange 3111. The engaging panels 3110 are formed around the outer surface of the engaging end 311 and are spaced apart from each other at intervals. The engaged flange 3111 is barbed, is formed on the outer surface of the engaging end 311 behind the engaging panels 3110, and selectively engages the retaining flange 2440. The depressed gap 313 is annularly formed in the outer surface of the pulling rod 31 adjacent to the engaged flange 3111 to serve as a forcing point for breaking the pulling rod 31. Then, the pulling rod 31 can be broken at the position of the depressed gap 313.

The gripping end 312 is formed on the rear end of the pulling rod 31, is opposite to the engaging end 311, and extends out of the pushrod chamber 210 through the holding tube 244 of the end cover 24. The gripping end 312 has an outer surface and multiple annular notches 3120. The annular notches 3120 are formed in the outer surface of the gripping end 312 and spaced apart at intervals to increase the friction when pulling the pulling rod 31.

With reference to FIGS. 1, 1B, and 2, the airtight spigot 32 is connected to the engaging end 311 of the pulling rod 31 and has a front end, a rear end, an outer surface, a connecting segment 321, a connecting recess 322, and an annular groove 323. The connecting segment 321 is formed on the front end of the airtight spigot 32 and is selectively mounted in the unplug recess 234 of the inner airtight stopper 23. The connecting recess 322 is centrically formed in the rear end of the airtight spigot 32, and has an inner wall, a diameter, and a holding flange 3220. The holding flange 3220 is formed in the inner wall of the connecting recess 322, has a diameter larger than the diameter of the connecting recess 322, and engages one of the engaging panels 3110 to provide a preferred fixing effect to the airtight spigot 32. The annular groove 323 is annularly formed in the outer surface of the airtight spigot 32, and selectively engages the second interior ring 218 to hold the airtight spigot 32 at a position of the second interior ring 218 by the annular groove 323.

With reference to FIGS. 1, 1A, and 2, the needle group 40 is connected to the needle-group mounting end 11 of the barrel 10, and has a needle 41, a needle seat 42, and a needle-seat fixing ring 43. The needle 41 has an inner end and an outer end. The inner end of the needle 41 is centrically mounted in the barrel lumen 13 of the barrel 10. The outer end of the needle 41 extends out of the barrel 10 via the needle-extending hole 110. The needle seat 42 is cylindrical, is mounted around the needle 41 at the inner end of the needle 41, and is centrically mounted in the barrel lumen 13 adjacent to the needle-seat holding hole 114 and the ribs 113. The needle seat 42 has a front end, a rear end, a center, an outer surface, a fixing hole 421, an engaging portion 422, and a protruding portion 423. The front end of the needle seat 42 is held in the small-diameter section 102, is mounted in the needle-seat holding hole 114 between the ribs 113 and faces the abutting step flange 112 by the triggering facilitating gap 111. The rear end of the needle seat 42 extends into the barrel lumen 13 of the large-diameter section 101. The fixing hole 421 is formed through the front end and the rear end of the needle seat 42, and airtightly secures the inner end of the needle 41. The engaging portion 422 is a step-shaped cylinder, is formed on and protrudes from the rear end of the needle seat 42, and is selectively mounted in the connecting segment 233 of the inner airtight stopper 23. The engaging portion 422 has an outer surface and a cutting slot 4220. The cutting slot 4220 is formed through the outer surface of the engaging portion 422 and communicates with the fixing hole 421 of the needle seat 42. The cutting slot 4220 can be used to discharge drug via the needle 41 from the barrel 10. The protruding portion 423 is formed on the outer surface of the needle seat 42 adjacent to the engaging portion 422.

The needle-seat fixing ring 43 is a hollow cylindrical elastomer, is airtightly mounted around the needle seat 42, and has a rear side, an outer surface, an abutting face 431, a holding recess 432, and an airtight fixing hole 433. The abutting face 431 is formed on the rear side of the needle-seat fixing ring 43. The holding recess 432 is formed in the outer surface of the needle-seat fixing ring 43 and airtightly engages the engaging flange 130 of the barrel lumen 13. The airtight fixing hole 433 is formed through the needle-seat fixing ring 43, and airtightly engages the protruding portion 423 to securely hold the needle seat 42 by the needle-seat fixing ring 43.

The needle cap 50 is detachably mounted around the needle-group mounting end 11 of the barrel 10 to cover the needle 41 of the needle group 40 to prevent the medical personnel from inadvertently contacting the needle 41.

In use, with reference to FIGS. 3, 3A, and 3B, the pulling rod 31 of the retracting element 30 is moved backwardly relative to the pushing element 20 by a user pulling the pulling rod 31. Then, the airtight spigot 32 is moved concomitantly with the pulling rod 31 from an initial position adjacent to the inner airtight stopper 23 along the pushrod chamber 210 of the pushing rod 21 to a destined rearward position by an external force. When the airtight spigot 32 is airtightly moved apart from the inner airtight stopper 23 in the pushrod chamber 210, the airtight spigot 32 can remove air in the pushrod chamber 210 until the airtight spigot 32 moves to a selected position in the pushing rod 21. With reference to FIG. 3C, as the airtight spigot 32 moves at the rear end of the pushing rod 21, the engaged flange 3111 of the pulling rod 31 securely engages the retaining flange 2440 of the end cover 24 to hold the pulling rod 31 with the end cover 24.

With reference to FIGS. 4, 4A, and 4B, when the pulling rod 31 is held on the end cover 24, the depressed gap 313 of the pulling rod 31 moves out of the end cover 24 adjacent to the cover bottom 243. With reference to FIG. 4C, the user can apply a lateral force on the pulling rod 31 to break the pulling rod 31 from the depressed gap 313, and the engaging end 311 carrying the airtight spigot 32 is securely positioned at the rear end of the pushing rod 21 in the pushrod chamber 210. Then, a selected low pressure condition is formed in the pushrod chamber 210 of the pushing rod 21, and the feature of the safety syringe A becomes the ones of functionally alike a conventional syringe additionally featured with a potential vacuum driving force that virtually hidden in the pushrod chamber 210.

With reference to FIGS. 5, 5A, 5B, 5C, 6, 6A, and 6B, the user can separate the needle cap 50 from the barrel 10 and insert the needle 41 into a medicine vial to extract the drug 60. Then, the user can push the pushing element 20 to move relative to the barrel 10 to inject the drug 60 into a human body via the needle 41.

Figure 7B:
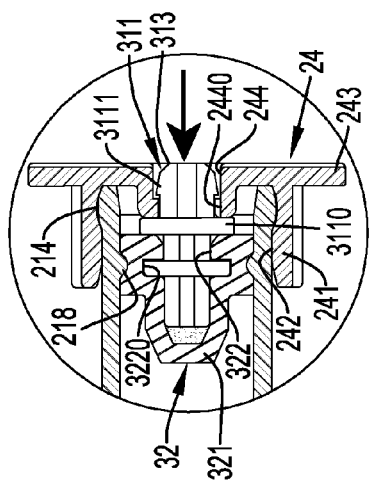
FIGS. 7A and 7B are operational and cross sectional side views of the safety syringe in FIG. 7.
Figure 7A:
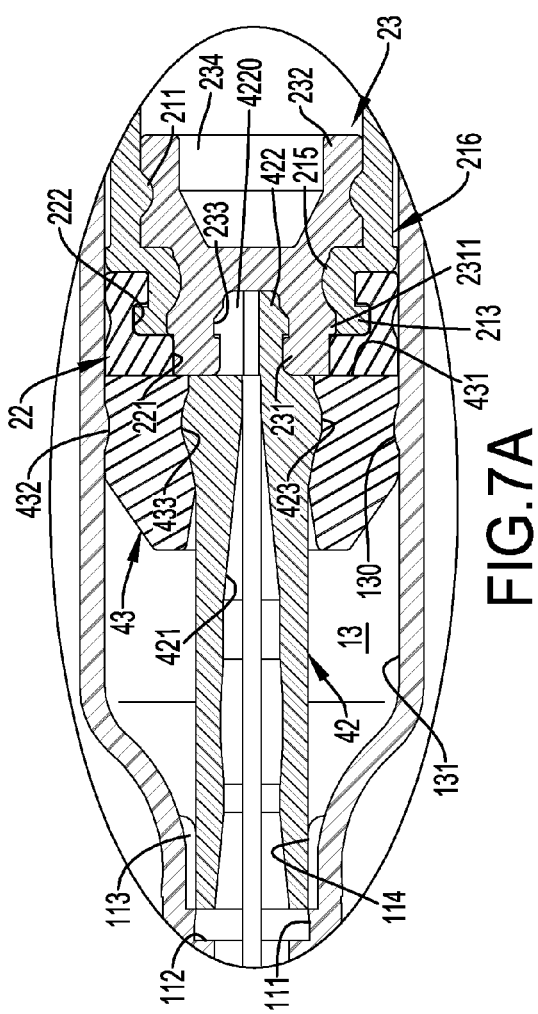
Figure 7:
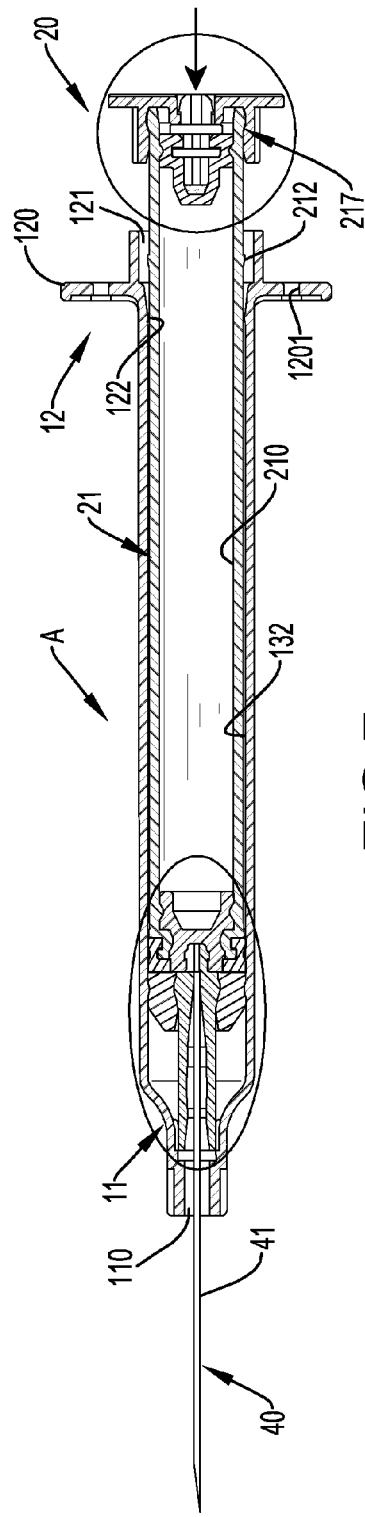
FIG. 7 is an operational and cross sectional side view of the safety syringe in FIG. 6, showing a needle seat fixing ring is pushed by the pushing element.

With reference to FIGS. 7, 7A, and 7B, on finishing the injection, the needle-seat fixing ring 43 is airtightly abutted against the outer airtight stopper 22, and the needle seat 42 is airtightly fitted with the inner airtight stopper 23, the drug solution 60 can be injected into the human body in complete and few of the residual drug solution 60 remains in the safety syringe A.

When the drug 60 is completely injected into the human body and further advancing the pushing element 20, a front side of the pushing element 20 is pushed forward to abut against the rear side of the needle-seat fixing ring 43 of the needle group 40, and the engaging portion 422 of the needle seat 42 tightly engages the connecting segment 233 of the inner airtight stopper 23. With reference to FIGS. 7, 7A, and 7B, the front end of the needle seat 42 is moved into the triggering facilitating gap 111 and abuts against the abutting step flange 112. Simultaneously, the holding recess 432 of the needle-seat fixing ring 43 disengages from the engaging flange 130 of the barrel lumen 13. When the pushing element 20 continuously moves forward, the needle-seat fixing ring 43 is pushed to move into the needle-seat positioning segment 131 and to release the airtight engagement with the needle seat 42. In addition, the inner airtight stopper 23 of the pushing element 20 disengage from the front drug pushing end 216 of the pushing rod 21 to release the airtight engagement between the inner airtight stopper 23 and the front drug pushing end 216. The pushing element 20 is moved forward until the end cover 24 abuts against the entry end 121 as shown in FIGS. 8, 8A, and 8B. The needle seat 42 that engages the inner airtight stopper 23 is moved in connection with the secured needle 41 into the pushrod chamber 210 under the low pressure condition that provides a vacuum suction force. With reference to FIGS. 9, 9A, 9B, and 9C, the low pressure condition of the pushrod chamber 210 enable an external atmospheric pressure to push the needle seat 42 and the inner airtight stopper 23 with the needle 41 simultaneously moving into the pushrod chamber 210, and this can provide an automatically retracting effect to the needle 41 and the needle seat 42.

Thus, in the present invention, the operation of the retracting element 30 can instantly form a low pressure condition in the pushing element 20. When finishing the injection, the user only needs to push the pushing element 20 forward, and this action enables the needle seat 42 securing the needle 41 to move rearward into the pushrod chamber 210 by the pressure difference between the low pressure of the pushrod chamber 210 and the ambient atmospheric pressure. Then, the user can retract the needle 41 into the pushrod chamber 210 directly in use, and this also can simplify the manufacturing process of the safety syringe A to reduce the cost of production when comparing with a conventional automated safety syringe using a stainless steel spring as the retraction force. In addition, the user does not need to run the risk of contacting the needle 41 when recycling or discarding the used needle 41 and this has a practical value.

Figure 10:
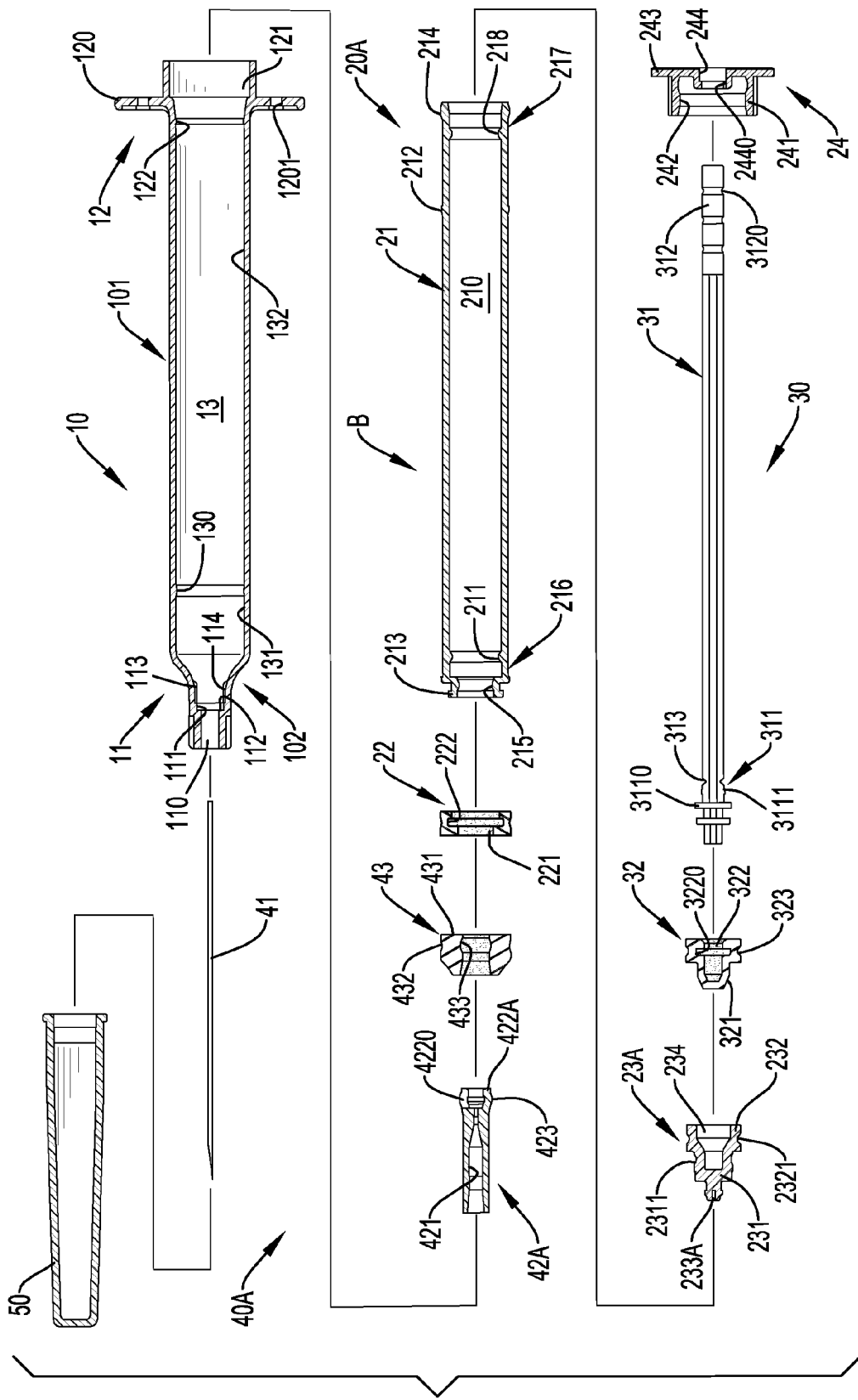
FIG. 10 is an exploded cross sectional side view of a second embodiment of a safety syringe in accordance with the present invention.
Figure 14B:
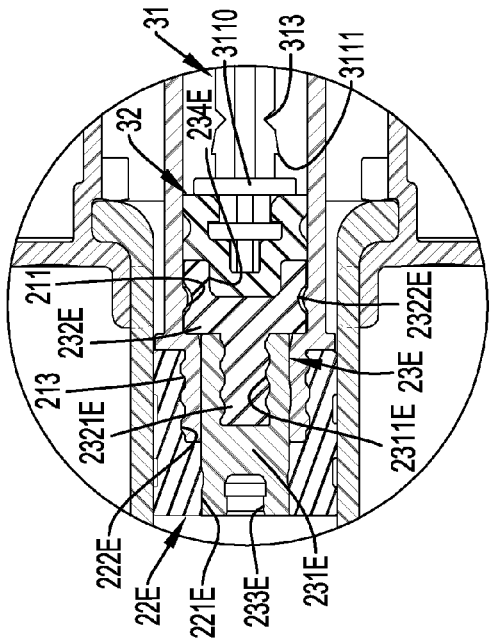
FIGS. 14A and 14B are enlarged and cross sectional side views of the safety syringe in FIG. 14.
Figure 14A:
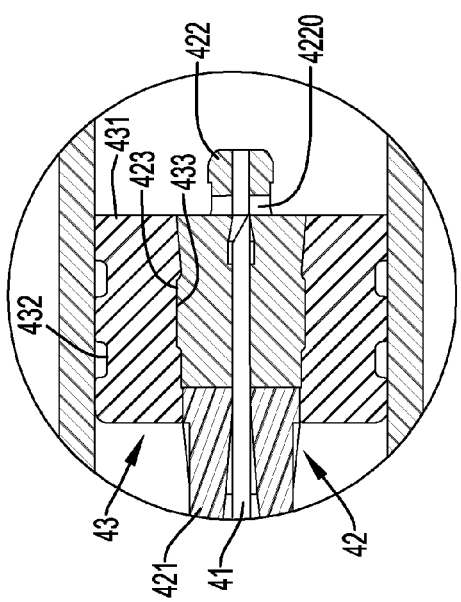
Figure 14:
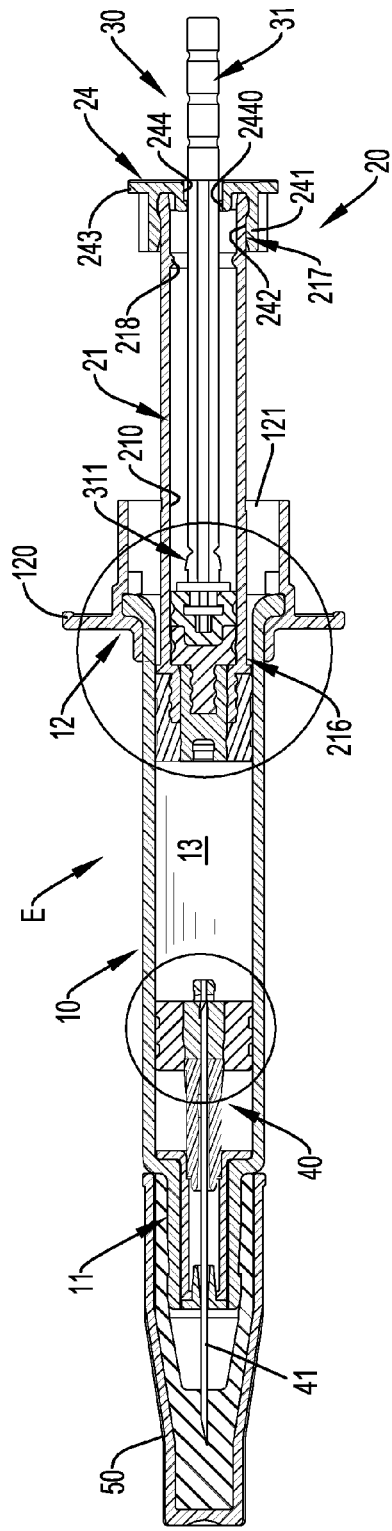
FIG. 14 a cross sectional side view of a sixth embodiment of a safety syringe in accordance with the present invention.

With reference to FIG. 10, a second embodiment of a safety syringe B in accordance with the present invention is substantially the same as the first embodiment except for the following features of the inner airtight stopper 23A of the pushing element 20A and the needle seat 42A of the needle group 40A. The connecting segment 233A of the inner airtight stopper 23A is cylindrical and is centrically formed on and protrudes from the front end of the inner airtight stopper 23A. The engaging portion 422A of the needle seat 42A is shaped as a round recess, is formed in the rear end of the needle seat 42A, and is corresponding to and mounted around the connecting segment 233A of the inner airtight stopper 23A. In addition, the other features and operation of the second embodiment of the safety syringe B are the same as those of the first embodiment of the safety syringe A.

With reference to FIGS. 11 and 11A, a third embodiment of a safety syringe B in accordance with the present invention is substantially the same as the second embodiment except for the injection volume of the third embodiment of the safety syringe B is about 5 cubic centimetes (C.C.). In addition, the other features and operation of the third embodiment of the safety syringe B are the same as those of the first embodiment of the safety syringe A.

With reference to FIGS. 12 and 12A, a fourth embodiment of a safety syringe C in accordance with the present invention is substantially the same as the first embodiment except for the following features. The injection volume of the safety syringe C is about 1 cubic centimetes (C.C.). The outer airtight stopper 22 is airtightly connected to the front drug pushing end 216 and is airtightly mounted around the protruding segment 231 of the inner airtight stopper 23. Furthermore, the other features and operation of the fourth embodiment of the safety syringe C are the same as those of the first embodiment of the safety syringe A.

With reference to FIGS. 13, 13A, 13B, and 13C, a fifth embodiment of a safety syringe D in accordance with the present invention is substantially the same as the first embodiment except for the injection volume of the safety syringe D is about 0.5 cubic centimetes (C.C.). Since a diameter of the barrel 10 is smaller, the inner airtight stopper 23D has multiple airtight rings 235 mounted around the engaging segment 232 to be airtightly mounted in the pushing rod 21. Then, the inner airtight stopper 23D can be airtightly moved in the pushrod chamber 210 of the pushing rod 21. Furthermore, the airtight spigot 32D that is mounted around the front end of the pulling rod 31D is annular and is airtightly and slidably mounted in the pushrod chamber 210 of the pushing rod 21. Additionally, the other features and operation of the fifth embodiment of the safety syringe D are the same as those of the first embodiment of the safety syringe A.

With reference to FIGS. 14, 14A, 14B, 15, 15A, and 15B, a sixth embodiment of a safety syringe E in accordance with the present invention is substantially the same as the first embodiment except for the following features. The inner airtight stopper 23E is composed of a protruding section 231E and an engaging section 232E. The protruding section 231E is threaded with the engaging section 232E. The outer airtight stopper 22E of the pushing element 20 is airtightly threaded with the front drug pushing end 216, and airtightly engages the protruding section 231E of the inner airtight stopper 23E, and is airtightly moved in the barrel lumen 13. The protruding section 231E has an outer wall airtightly engaging the outer airtight stopper 22E, and the connecting segment 233 is formed on a front side of the protruding section 231E. Furthermore, the protruding section 231E has a rear side and a threaded portion 2311E formed in the rear side of the protruding section 231E. The engaging section 232E has a front side, an outer wall, a screwed portion 2321E, and an annular trough 2322E. The screwed portion 2321E is formed on and protrudes from the front side of the engaging section 232E and is securely threaded with the threaded portion 2311E of the protruding section 231E. The annular trough 2322E is formed in the outer wall of the engaging section 232E and airtightly engages the first interior ring 211 of the pushing rod 21. Additionally, the other features and operation of the sixth embodiment of the safety syringe E are the same as those of the first embodiment of the safety syringe A.

According to the above-mentioned features and structural relationships of the safety syringe A, B, C, D, E in accordance with the present invention, the retracting element 30 is mounted in the pushing element 20, and can be manually pulled to move rearward relative to the pushing element 20 to instantly form a low pressure condition of selective intensity in the pushing element 20 to provide a vacuum attraction force. The pushing element 20 is pushed at a proper position during the injecting process, the needle 41 and the needle seat 42 are connected to the inner airtight stopper 23, 23A, 23D, 23E and are synchronously moved into the pushrod chamber 210 by the ambient atmospheric pressure, and this can retract the needle 41 automatically and safely. Furthermore, the components of the safety syringe A, B, C, D, E can engage or disengage each other by structures of projections and the relative depressions structure, and this can simplify the internal structures of the safety syringe A, B, C, D, E. The manufacturing process of the safety syringe A, B, C, D, E can be simplified by averting the conventionally use of a stainless spring as the driving force to move the used needle so as to reduce the cost of production and enhance the eco-friendly advantage of the syringe usage, and this has a practical value.

Even though numerous characteristics and advantages of the present invention have been set forth in the foregoing description, together with details of the structure and function of the invention, the disclosure is illustrative only, and changes may be made in detail, especially in matters of shape, size, and arrangement of parts within the principles of the invention to the full extent indicated by the broad general meaning of the terms in which the appended claims are expressed.

What is claimed is:

1. A safety syringe comprising:
   a barrel being a hollow cylinder and having
      an inner wall;
      a large-diameter section having a front end and a rear end;
      a small-diameter section in a tapered-shape, formed on and protruding from the front end of the large-diameter section;
      a needle-group mounting end extending from the large-diameter section to the small-diameter section;
      an operating grip end defined at the rear end of the large-diameter section and opposite to the needle-group mounting end; and
      a barrel lumen in the large-diameter section of the barrel and having an engaging flange formed on and protruding from the inner wall of the barrel adjacent to the needle-group mounting end;
   a pushing element airtightly and slidably mounted in the barrel lumen of the barrel, and having
      a pushing rod having
         a pushrod chamber formed in the pushing rod;
         a front drug pushing end slidably mounted in the barrel lumen; and
         a rear operating end being opposite to the front drug pushing end and extending out of the barrel lumen;
      an inner airtight stopper airtightly and securely mounted in the front drug pushing end of the pushing rod, and extending into and airtightly mounted in the pushrod chamber;
      an outer airtight stopper securely connected to the front drug pushing end and the inner airtight stopper, and airtightly and slidably mounted in the barrel lumen; and
      an end cover securely mounted on the rear operating end of the pushing rod and having a holding tube formed on and through a center of the end cover;
   a retracting element airtightly and slidably mounted in the pushrod chamber of the pushing rod and having
      a pulling rod having
         a gripping end extending out of the pushrod chamber through the holding tube of the end cover; and
         an engaging end being opposite to the gripping end and extending in the pushrod chamber; and
      an airtight spigot securely connected to the engaging end of the pulling rod and adjacent to the inner airtight stopper;
   a needle group connected to the needle-group mounting end of the barrel, and having
      a needle having
         an outer end extending out of the needle-group mounting end; and
         an inner end mounted in the needle-group mounting end;

a needle seat mounted around the needle at the inner end of the needle, mounted in the needle-group mounting end of the barrel, and having
a front end being held in the small-diameter section;
a rear end extending into the barrel lumen of the large-diameter section; and
an engaging portion formed on the rear end of the needle seat and detachably engaging the inner airtight stopper of the pushing element; and
a needle-seat fixing ring mounted around the needle seat and airtightly engaging the engaging flange in the large-diameter sect and
wherein the pulling rod of the retracting element is moved backwardly relative to the pushing element by pulling the pulling rod, the airtight spigot is airtightly moved with the pulling rod apart from the inner airtight stopper along the pushrod chamber of the pushing rod to remove air in the pushrod chamber until the airtight spigot moves to a selected position of the pushing rod, a low pressure condition of selected intensity is formed in the pushrod chamber of the pushing rod, wherein after an injection process the pushing element is pushed forward to abut and move the needle-seat fixing ring, the needle-seat fixing ring is moved to disengage sequentially from the engaging flange of the barrel and the needle seat, the needle seat and the inner airtight stopper are moved into the pushing rod concomitantly, and a pressure difference between the low pressure condition of the pushrod chamber and the ambient atmospheric pressure attracts the inner airtight stopper and the needle seat that carries the needle simultaneously into the pushrod chamber to provide an automatically retracting effect to the needle and the needle seat.

2. The safety syringe as claimed in claim 1, wherein
the inner airtight stopper has a connecting segment being grooved and formed in a front end of the inner airtight stopper; and
the engaging portion of the needle seat is a step-shaped cylinder, is formed on and protrudes from the rear end of the needle seat, and is corresponding to engage the connecting segment of the inner airtight stopper.

3. The safety syringe as claimed in claim 1, wherein
the inner airtight stopper has a connecting segment being cylindrical, formed on and protruding from a front end of the inner airtight stopper; and
the engaging portion of the needle seat is shaped as a round recess, is formed in the rear end of the needle seat, and is corresponding to and mounted around the connecting segment of the inner airtight stopper.

4. The safety syringe as claimed in claim 1, wherein
the small-diameter section of the barrel has
a needle-extending hole formed through the small-diameter section, communicating with the barrel lumen in the large-diameter section, and having an inner diameter;
a needle-seat holding hole formed in an annular wall of the small-diameter section behind the needle-extending hole, and having an inner diameter larger than the inner diameter of the needle-extending hole; and
an abutting step flange formed in the annular wall of the small-diameter section between the needle-extending hole and the needle-seat holding hole; and
the outer end of the needle extends out of the needle-group mounting end via the needle-extending hole.

5. The safety syringe as claimed in claim 4, wherein the small-diameter section of the barrel has a triggering facilitating gap formed in the small-diameter section between the abutting step flange and a front end of the needle-seat holding hole to provide a facilitating effect of triggering an initial movement of the needle seat after use of the safety syringe.

6. The safety syringe as claimed in claim 1, wherein the pushing rod has a first interior ring annularly formed on and protruding from an inner wall of the pushing rod adjacent to the front drug pushing end.

7. The safety syringe as claimed in claim 6, wherein
the inner airtight stopper is a step block and has
a protruding segment formed on a front end of the inner airtight stopper, airtightly and securely connected to the front drug pushing end, and having a diameter;
an engaging segment formed on a rear end of the inner airtight stopper, formed with the protruding segment, and having
a diameter larger than the diameter of the protruding segment;
an outer wall; and
an annular recess annularly formed on the outer wall of the engaging segment, and airtightly engaging the first interior ring of the pushing rod; and
an unplug recess formed in a rear side of the engaging segment; and
the inner airtight stopper has a connecting segment formed in a front side of the protruding segment.

8. The safety syringe as claimed in claim 7, wherein
the pushing rod has a mounting segment formed around the front drug pushing end; and
the outer airtight stopper is mounted around the mounting segment of the pushing rod, is airtightly connected to the protruding segment of the inner airtight stopper, is airtightly and slidably mounted in the barrel lumen of the barrel, and selectively abuts a rear side of the needle-seat fixing ring of the needle group.

9. The safety syringe as claimed in claim 7, wherein the outer airtight stopper of the pushing element is airtightly connected to the front drug pushing end, is airtightly connected to the protruding segment of the inner airtight stopper, and is airtightly and slidably mounted in the barrel lumen of the barrel.

10. The safety syringe as claimed in claim 7, wherein
the front drug pushing end of the pushing rod has a screwed segment; and
the outer airtight stopper is airtightly screwed with the screwed segment of the front drug pushing end, is airtightly connected to the protruding segment of the inner airtight stopper, and is airtightly and slidably mounted in the barrel lumen of the barrel.

11. The safety syringe as claimed in claim 7, wherein
the pushing rod has an inner ring annularly formed in the front drug pushing end; and
the protruding segment of the inner airtight stopper has
an outer wall; and
a concave groove annularly formed on the outer wall of the protruding segment, and airtightly engaging the inner ring of the front drug pushing end of the pushing rod.

12. The safety syringe as claimed in claim 11, wherein
the inner airtight stopper is composed of a protruding section and an engaging section;
the protruding section has
an outer wall airtightly engaging the outer airtight stopper;
a rear side; and
a threaded portion formed in the rear side of the protruding section;

the engaging section is threaded with the protruding section to form the inner airtight stopper, and has
  a front side;
  an outer wall;
    a screwed portion formed on and protruding from the front side of the engaging section and securely threaded with the threaded portion of the protruding section; and
    an annular trough formed in the outer wall of the engaging section and airtightly engaging the first interior ring of the pushing rod in the pushrod chamber; and
the connecting segment is centrically formed on a front side of the protruding section.

13. The safety syringe as claimed in claim 6, wherein
the pulling rod is an elongated rod with multiple protruding ribs formed on an outer surface of the pulling rod, and has a front end and a rear end;
the engaging end of the pulling rod is formed on the front end of the pulling rod and has
  an outer surface; and
    multiple engaging panels formed around the outer surface of the engaging end and spaced apart at intervals; and the gripping end is formed on the rear end of the pulling rod, is opposite to the engaging end, and extends out of the pushrod chamber via the end cover; and
the pulling rod has a depressed gap annularly formed in the outer surface of the pulling rod to serve as a forcing point for breaking the pulling rod.

14. The safety syringe as claimed in claim 13, wherein
the holding tube of the end cover has
  an inner end; and
    a retaining flange formed on and protruding from the inner end of the holding tube; and
the engaging end of the pulling rod has an engaged flange formed on the outer surface of the engaging end between the engaging panels and the depressed gap, and selectively engaging the retaining flange of the holding tube of the end cover.

15. The safety syringe as claimed in claim 14, wherein the low pressure condition in the pushrod chamber is formed by a movement of the engaging end of the pulling rod engaging the airtight spigot, the retracting element moving backward by pulling the gripping end, and the engaging end of the pulling rod engaging the retaining flange of the holding tube of the end cover.

* * * * *